(12) United States Patent
Farzin-Nia et al.

(10) Patent No.: US 8,672,676 B2
(45) Date of Patent: Mar. 18, 2014

(54) ARCHWIRE ASSEMBLY WITH STOPS

(75) Inventors: Farrokh Farzin-Nia, Inglewood, CA (US); Todd I. Oda, Torrance, CA (US)

(73) Assignee: Ormco Corporation, Orange, CA (US)

( * ) Notice: Subject to any disclaimer, the term of this patent is extended or adjusted under 35 U.S.C. 154(b) by 0 days.

(21) Appl. No.: 13/476,777

(22) Filed: May 21, 2012

(65) Prior Publication Data

US 2012/0231409 A1 Sep. 13, 2012

Related U.S. Application Data

(60) Continuation of application No. 11/566,395, filed on Dec. 4, 2006, now abandoned, which is a division of application No. 10/790,413, filed on Mar. 1, 2004, now Pat. No. 7,160,106.

(51) Int. Cl.
*A61C 3/00* (2006.01)
(52) U.S. Cl.
USPC .......................................................... 433/22
(58) Field of Classification Search
USPC ..................................................... 433/20, 22
See application file for complete search history.

(56) References Cited

U.S. PATENT DOCUMENTS

| | | | |
|---|---|---|---|
| 1,361,661 A | 12/1920 | Alexander | |
| 2,318,001 A | 5/1943 | Linde | |
| 3,158,934 A | 12/1964 | Waldman | |
| 3,683,502 A | 8/1972 | Wallshein | |
| 3,758,947 A | 9/1973 | Kesling | |
| 4,097,993 A | 7/1978 | Andrews | |
| 4,202,100 A | 5/1980 | Forster | |
| 4,526,540 A | 7/1985 | Dellinger | |
| 4,571,179 A | 2/1986 | Balenseifen | |
| 4,583,944 A | 4/1986 | Hanson | |
| 4,639,219 A * | 1/1987 | Gagin | 433/22 |
| 4,764,112 A * | 8/1988 | Bergersen | 433/22 |
| 4,900,251 A | 2/1990 | Andreasen | |
| 5,112,221 A | 5/1992 | Terry | |
| 5,154,613 A | 10/1992 | Cohen | |
| 5,240,413 A * | 8/1993 | Ashinoff | 433/24 |
| 5,259,760 A | 11/1993 | Orikasa | |
| 5,306,142 A * | 4/1994 | Richards | 433/22 |
| 5,317,074 A | 5/1994 | Hammar et al. | |

(Continued)

OTHER PUBLICATIONS

Bead and Button Projects, 132 Tips and Techniques, pp. 4 and 5, copyright 2003, available on Google Books.*

(Continued)

*Primary Examiner* — Ralph Lewis
(74) *Attorney, Agent, or Firm* — Wood, Herron & Evans, LLP

(57) ABSTRACT

An archwire assembly comprises an archwire with a crimpable sleeve adapted to slidably move along the archwire so as to be positioned between two adjacent brackets of orthodontic braces. The archwire assembly further includes a stop applied to the archwire and adapted to limit the movement of the sleeve along the archwire. The stop may include removable stops where the sleeve is movable along the archwire between the stops. The removable stops may be movable along the archwire with the application of a sufficient force. The stop may also include a friction-creating substance applied to either the sleeve or the archwire such that it takes a sufficient force to move the sleeve along the archwire. The stop may also include a partially crimped sleeve applied to the archwire such that it takes a sufficient force to move the sleeve along the archwire.

10 Claims, 4 Drawing Sheets

(56) References Cited

U.S. PATENT DOCUMENTS

| | | | |
|---|---|---|---|
| 5,380,197 | A | 1/1995 | Hanson |
| 5,655,653 | A | 8/1997 | Chester |
| 5,766,005 | A | 6/1998 | Casey |
| 5,910,008 | A | 6/1999 | Tran |
| 6,203,317 | B1 | 3/2001 | Davanathan |
| 6,425,758 | B1 | 7/2002 | Forster |
| 7,051,414 | B2 | 5/2006 | Swanson |
| 7,160,106 | B2 | 1/2007 | Farzin-Nia et al. |

OTHER PUBLICATIONS

U.S. Patent and Trademark Office, Office Action in U.S. Appl. No. 10/790,413, dated Jan. 11, 2006.
U.S. Patent and Trademark Office, Office Action in U.S. Appl. No. 11/566,395, dated Mar. 31, 2008.
U.S. Patent and Trademark Office, Office Action in U.S. Appl. No. 11/566,395, dated Oct. 20, 2008.
U.S. Patent and Trademark Office, Office Action in U.S. Appl. No. 11/566,395, dated Apr. 14, 2009.
U.S. Patent and Trademark Office, Office Action in U.S. Appl. No. 11/566,395, dated Nov. 13, 2009.
U.S. Patent and Trademark Office, Board of Patent Appeals and Interferences, Decision on Appeal in U.S. Appl. No. 11/566,395 (Appeal No. 2010-011261), dated Mar. 20, 2012.
U.S. Patent and Trademark Office, Examiner's Answer in U.S. Appl. No. 11/566,395, dated May 25, 2010.
U.S. Patent and Trademark Office, Office Action in U.S. Appl. No. 11/942,246, dated Oct. 1, 2009.
U.S. Patent and Trademark Office, Office Action in U.S. Appl. No. 11/942,246, dated Mar. 16, 2010.
U.S. Patent and Trademark Office, Office Action in U.S. Appl. No. 11/942,246, dated Mar. 3, 2011.
U.S. Patent and Trademark Office, Advisory Action in U.S. Appl. No. 11/942,246, dated May 27, 2010.
U.S. Patent and Trademark Office, Notice of Allowance in U.S. Appl. No. 10/790,413, dated Sep. 27, 2006.
U.S. Patent and Trademark Office, Notice of Allowance in U.S. Appl. No. 10/790,413, dated Nov. 29, 2006.
Bead and Button Projects, Easy-Does-It Series, 132 Tips and Techniques, pp. 4 and 5, Kalmbach Publishing, 2003, available on Google Books.

* cited by examiner

ARCHWIRE ASSEMBLY WITH STOPS

CROSS-REFERENCE TO RELATED APPLICATION

This application is a continuation application of pending U.S. patent application Ser. No. 11/566,395, filed on Dec. 4, 2006, which is a divisional application of U.S. patent application Ser. No. 10/790,413, filed on Mar. 1, 2004 and issued as U.S. Pat. No. 7,160,106 on Jan. 9, 2007, the disclosures of which are incorporated by reference herein in their entireties.

FIELD OF THE INVENTION

The invention relates to orthodontic devices, and more particularly, to a device used in conjunction with archwires employed in orthodontic procedures.

BACKGROUND OF THE INVENTION

Orthodontic treatment normally involves the application of mechanical forces to urge improperly positioned teeth into correct alignment. One common form of orthodontic treatment includes the use of orthodontic brackets that are fixed to teeth such as by a band around individual teeth or, perhaps more commonly, by adhering the brackets directly to the teeth. A resilient curved archwire is then seated in the archwire slots of the brackets. The archwires are generally attached to the brackets by ligature wires or elastic bands. In some cases, however, self-ligating brackets are used that include a movable cover that selectively closes the labial side of the archwire slot of the brackets. The movable cover is opened for inserting the archwire and then closed for retaining the archwire within the archwire slot. When a patient's teeth are incorrectly leveled and aligned, the archwire elastically deforms to engage the brackets, thereby introducing a force that urges the teeth to move to the correct position over time.

A frequent problem observed during orthodontic treatment is that the archwire tends to move mesially-distally relative to the brackets. The archwire engaged with the bracket slots flexes under forces applied in the oral environment, such as forces applied for chewing and tongue, musculature actions, or orthodontic forces. These unbalanced forces have a tendency to move the archwire through the archwire slots of the brackets in a mesial-distal direction. This movement may cause a free end of the archwire to protrude from one of the brackets attached to the distalmost molars and contact gum or cheek tissue. As a result of the movement, the opposite free end of the archwire may also become disengaged from the bracket that is mounted to the distalmost molar on the opposite side of the mouth cavity. The contact leads to irritation of the gum or cheek tissue. Self-ligating brackets by definition lack structures, such as ligatures and elastic bands, that might limit the mesial-distal movement. Therefore, the mesial-distal movement of the archwire is more pronounced in both active and passive self-ligating brackets.

Several conventional techniques are used to limit the mesial-distal movement of the archwire in the bracket slots. One such technique, for example, is to insert the archwire through a crimpable sleeve, such as a small diameter tube, then position the archwire within the archwire slots with the sleeve located between two adjacent brackets. The sleeve is eventually secured to the archwire at a fixed position by crimping the sleeve to the archwire. The sleeve is configured such that the sleeve cannot pass through or move beyond an archwire slot as the archwire moves in the mesial-distal direction. In this manner, the maximum mesial-distal movement of the archwire is limited to the distance between the adjacent brackets. If the distance between adjacent brackets is sufficiently small, then the free ends of the archwire do not either become disengaged from the bracket or protrude from the bracket for irritating gum or cheek tissue.

A major shortcoming of the conventional technique described above is that the crimpable sleeve is mounted to the archwire in the field, such as a doctor's office, and usually by the dentist or a dental assistant. This field assembly process is often time consuming and may prove frustrating. An archwire has a small cross-sectional profile and a crimpable sleeve has a very small passageway for threading the archwire through the sleeve. Because of the small sizes, the sleeve is difficult to thread onto the archwire. Moreover, during handling of the archwire, such as during its installation into the patient's mouth, the sleeve often slides off one free end of the archwire and onto the floor, or is possibly lost into the patient's mouth. It is often difficult to find a sleeve on the floor after it has fallen off the end of the archwire.

There is thus a need for an improved archwire assembly that eliminates the field assembly and further limits the movement of the sleeve once positioned on the archwire.

SUMMARY OF THE INVENTION

The invention provides an improved archwire assembly without the drawbacks of existing archwire orthodontic devices. In one embodiment of the invention, the archwire assembly comprises an archwire, a crimpable sleeve adapted to slidably move along the archwire, and two removable stops positioned on opposed sides of the sleeve and adapted to limit the movement of the sleeve along the archwire. The removable stops may be placed adjacent the ends of the sleeve to substantially prevent the sleeve from moving along the archwire or may be placed adjacent to the ends of the archwire to prevent the sleeve from falling off the archwire. Furthermore, the removable stops may be movable along the length of the archwire when exposed to a sufficient force, such as a force greater than the weight of the sleeve. In this manner, the sleeve can be repositioned along the archwire to properly position it between adjacent brackets. The sleeve is eventually crimped to secure the sleeve to the archwire at a fixed position and the removable stops are then removed.

In another embodiment of the invention, the archwire assembly includes an archwire, a crimpable sleeve adapted to slidably move along the archwire, and a friction-creating substance applied to either the crimpable sleeve or to the archwire and adapted to limit movement of the sleeve along the archwire. The friction-creating substance creates friction between the sleeve and archwire such that it takes a sufficient force, such as a force greater than the weight of the sleeve, to move the sleeve along the archwire. Otherwise, the position of the sleeve remains stationary. In this manner, the sleeve can be repositioned along the archwire to properly position it between adjacent brackets. The sleeve is eventually crimped to secure the sleeve to the archwire at a fixed position. The friction-creating substance may be removable, such as by being water soluble, and removed after the sleeve is secured to the archwire.

In yet another embodiment of the invention, the archwire assembly includes an archwire and a crimpable sleeve that has been partially crimped so as to limit movement of the sleeve along the archwire. The sleeve is crimped just enough such that it takes a sufficient force, such as a force greater than the weight of the sleeve, to move the sleeve along the archwire. Otherwise, the position of the sleeve remains stationary.

In this manner, the sleeve can be repositioned along the archwire to properly position it between adjacent brackets. The sleeve is eventually completely crimped so as to secure the sleeve to the archwire at a fixed position.

By virtue of the foregoing, there is thus provided an archwire assembly that eliminates field assembly and further limits movement of the crimpable sleeve along the archwire. These and other advantages of the invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with the general description of the invention given above and the detailed description of the embodiments given below, serve to explain the principles of the invention.

DETAILED DESCRIPTION

Figure 1:
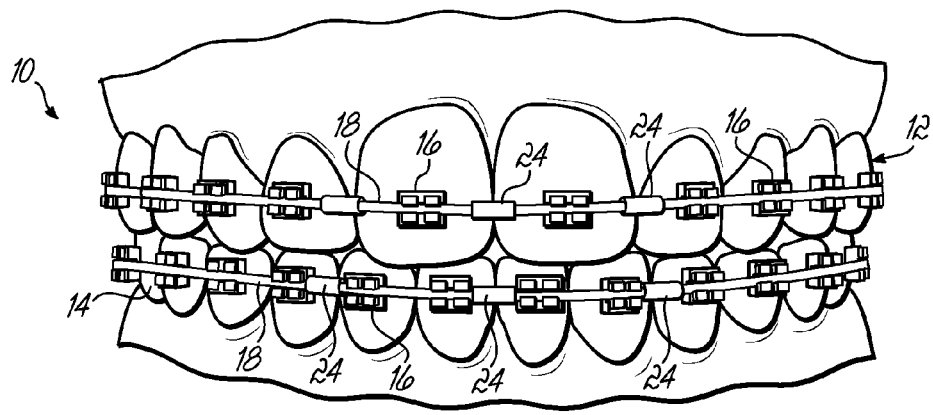
FIG. 1 is perspective view of orthodontic braces incorporating an archwire assembly according to the invention.
Figure 2:
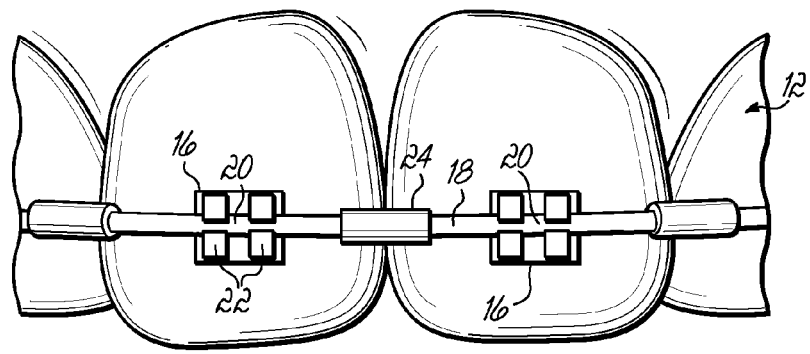
FIG. 2 is an enlarged view of a portion of FIG. 1.

With reference to FIGS. 1-2, orthodontic braces 10 are provided or applied on the upper teeth 12 and lower teeth 14. The braces 10 generally comprise brackets 16 typically adhered to the upper and lower teeth 12, 14. Archwires 18, which may be formed of NiTi alloys, Ti based alloys or stainless steel, are attached to brackets 16 along archwire slots 20 by, for example, ligature wires or elastic bands 22 or brackets 16 may be self-ligating. Braces 10 further include crimpable sleeves 24 positioned between adjacent brackets 16. Once positioned between adjacent brackets, sleeves 24 are crimped to secure sleeves 24 to the archwire 18 at a fixed position. Sleeves 24 are configured such that sleeves 24 cannot slide past archwire slots 20 of brackets 16 when the archwire 18 moves in a mesial-distal direction. The mesial-distal movement of the archwire 18 is then limited to the distance between adjacent brackets 16. When sleeves 24 contact brackets 16, any further movement of the archwire 18 is then prevented.

Figure 3:
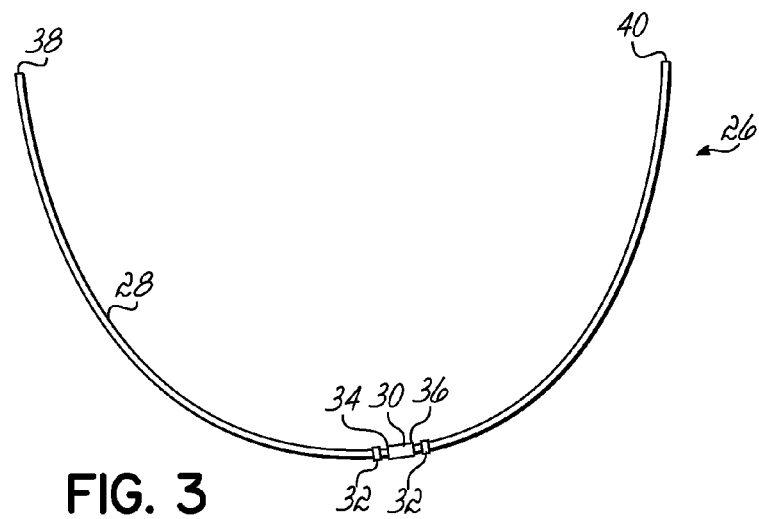
FIG. 3 is a top plan view of an embodiment of the archwire assembly according to the invention showing removable stops on the archwire.

With reference to FIG. 3, an archwire assembly, shown generally at 26, comprises an archwire 28 having a crimpable sleeve 30 applied in an uncrimped condition to archwire 28. The sleeve 30 is adapted to freely slide along the archwire 28 so as to be easily positioned at desired locations along the archwire 28, such as between a chosen pair of brackets 16 (FIG. 2). The archwire assembly 26 further includes removable stops 32 applied to the archwire 28 at opposed ends 34, 36 of sleeve 30 such that sleeve 30 is movable along the archwire 28 between removable stops 32. Stops 32 may be positioned immediately adjacent ends 34, 36 of sleeve 30 to substantially prevent sleeve 30 from moving along archwire 28. Alternatively, stops 32 may be positioned adjacent the ends 38, 40 of archwire 28. Sleeve 30 is then free to slide along substantially the entire length of archwire 28 but is prevented from sliding off ends 38, 40 of archwire 28 due to stops 32. It is to be understood, however, that stops 32 may be placed at any location along the archwire 28 that bound sleeve 30 between stops 32. The archwire assembly 26 may be pre-assembled and packaged for delivery to a doctor's office with the sleeve 30 and stops 32 already mounted on the archwire 28. This advantageously eliminates the frustrating and time consuming field assembly required to apply the sleeve 30 onto archwire 28 and limits its movement along archwire 28.

Figure 3A:
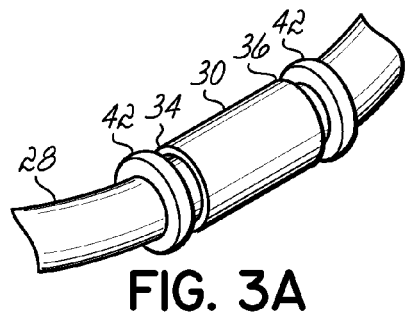
FIG. 3A is an enlarged view of a portion of FIG. 3 showing a pair of elastic O-rings as removable stops.
Figure 3B:
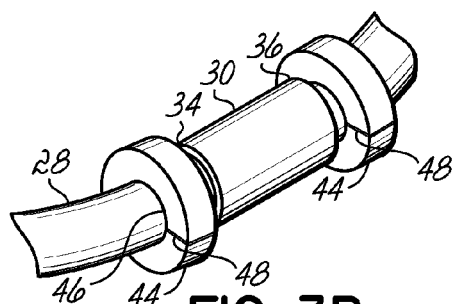
FIG. 3B is an enlarged view of an archwire assembly similar to FIG. 3A showing a pair of slotted collars as removable stops.
Figure 3C:
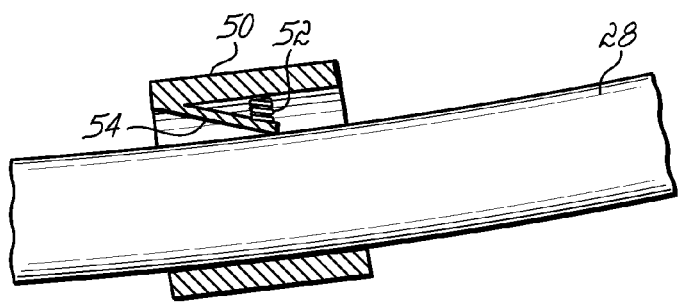
FIG. 3C is an enlarged cross sectional view of an archwire assembly similar to FIG. 3A showing a spring loaded stop as a removable stop.
Figure 3D:
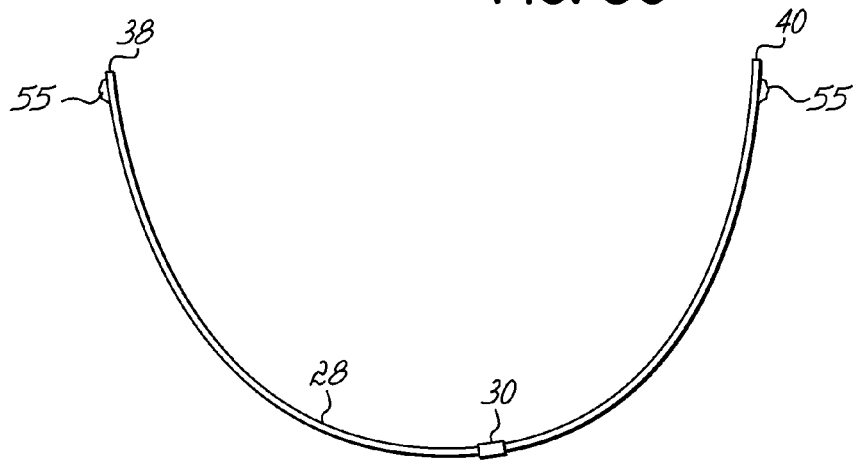
FIG. 3D is a top plan view of an archwire assembly similar to FIG. 3 showing discrete amounts of a substance at the ends of the archwire as the removable stops.

A wide range of removable stops 32 may be used in the invention. For example, FIG. 3A shows a pair of elastic O-rings 42 on archwire 28 and bounding sleeve 30 between the O-rings 42. FIG. 3B shows a pair of removable stops in the form of slotted collars 44 having a hole 46 therein to engage archwire 28 and further having a radial slot 48 such that stops 44 may be positioned on the archwire 28 by sliding archwire 28 through the radial slot 48 and into hole 46. Slotted collars 44 may be a resilient plastic material that engages archwire 28 or may be metallic stops that are crimped to engage archwire 28. FIG. 3C shows a spring loaded stop 50 comprising a spring 52 and arm 54 such that spring 52 engages arm 54 against archwire 28. FIG. 3D shows an archwire 28 having a sleeve 30 and further having discrete amounts 55 of a substance, such as an organic material, a polymeric material or a wax, situated at ends 38, 40 of archwire 28 that operate as removable stops 32 so that sleeve 30 cannot come off ends 38, 40 of the archwire 28.

Figure 3E:
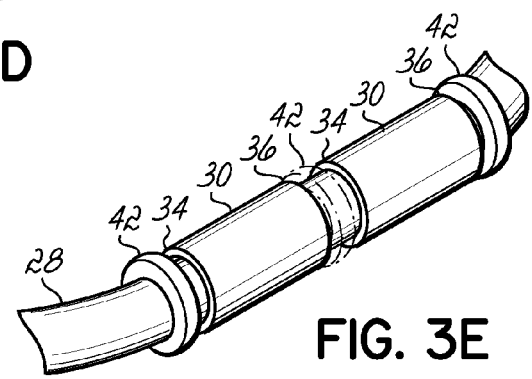
FIG. 3E is an enlarged view of an archwire assembly similar to FIG. 3A showing a second crimpable sleeve between removable stops.

It is to be understood that multiple sleeves and multiple stops may be used in an archwire assembly. For instance, and as shown in FIG. 3E, the archwire assembly 26 may have a second crimpable sleeve 31 between stops 32. Additionally, a third stop 33 (shown in phantom) may be positioned between stops 30, 31. Alternatively, an archwire assembly may provide several pre-applied sleeves with stops located only at the ends of the archwire. Those skilled in the art will recognize a wide range of configurations possible with the invention.

Stops 32 may be advantageously movable along archwire 28. This allows the dentist, or other clinician, to reposition sleeve 30 to a particular position along archwire 28 and then temporarily fix the location of the sleeve with removable stops 32. This might occur, for example, in positioning sleeve 30 between adjacent brackets 16. Removable stops 32 that are movable, such as for example, O-rings 42, slotted collars 44 and spring loaded stops 50 are adapted to move along archwire 28 only upon the application of a large enough force.

Otherwise, the position of removable stops 32 remains stationary. To prevent the unintentional movement of removable stops 32 along archwire 28, the force required to move removable stops 32 should be greater than the weight of sleeve 30. For example, removable stops 32 may be adapted to move on the application of a force of approximately one half pound. This prevents the movement of removable stops 32 under the weight of sleeve 30 but allows removable stops 32 to be easily repositioned along archwire 28. Once sleeve 30 has been properly positioned along archwire 28, such as between adjacent brackets 16, sleeve 30 is eventually crimped to secure sleeve 30 to archwire 28 at a fixed position. Removable stops 32 are then removed from archwire 28.

Figure 4:
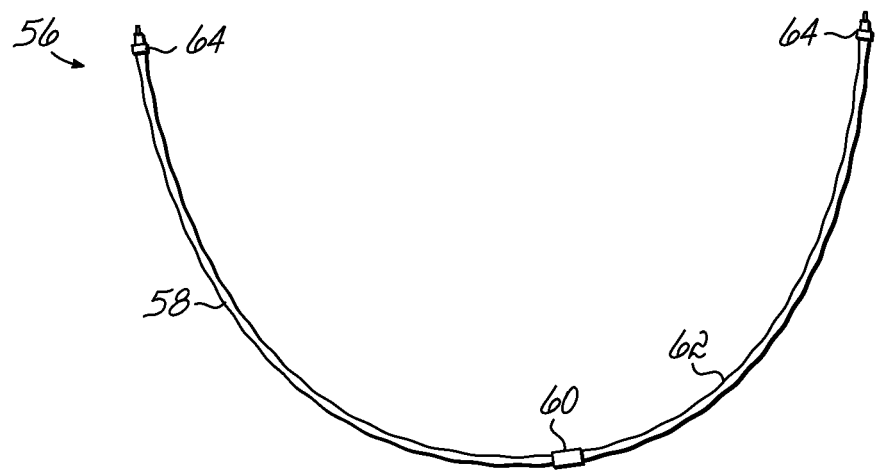
FIG. 4 is a top plan view of another embodiment of an archwire assembly according to the invention showing a friction-creating substance coating the archwire.
Figure 5:
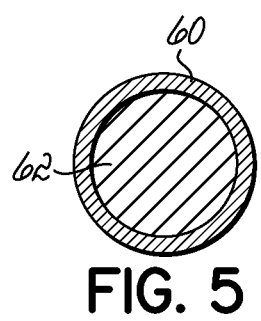
FIG. 5 is a side elevation cross sectional view of a sleeve filled with a friction-creating substance.
Figure 6:
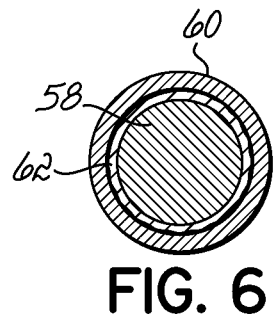
FIG. 6 is a side elevation cross sectional view of a sleeve on the archwire with a friction-creating coating therebetween.

With reference to FIGS. 4-6 and in another embodiment of the invention, an archwire assembly 56 comprises an archwire 58 having a crimpable sleeve 60 applied in an uncrimped condition to archwire 58. Archwire assembly 56 further includes a friction-creating substance 62 adapted to limit movement of sleeve 60 along archwire 58. As shown in FIG. 4, the friction-creating substance 62 may be applied to archwire 58 by either partially or completely coating archwire 58. Alternatively, and as shown in FIG. 5, the friction creating substance may be applied to the inside of sleeve 60, such as for example, by partially or completely filling sleeve 60 with the friction-creating substance 62.

In either case, and as shown in FIG. 6, the archwire assembly 56 includes a friction-creating substance 62 between the sleeve 60 and archwire 58. Sleeve 60, however, remains movable along archwire 58 upon the application of a large enough force. Otherwise, the position of sleeve 60 remains stationary. To prevent the unintentional movement of sleeve 60 along archwire 58, the force required to move sleeve 60 should be greater than the weight of sleeve 60. For example, sleeve 60 may be adapted to move on the application of a force of approximately one half pound. This prevents the movement of sleeve 60 under its own weight but allows sleeve 60 to be easily repositioned along archwire 58. Additionally, archwire assembly 56 may further include removable stops 64 as an additional feature to, for example, prevent sleeve 60 from coming off the archwire 58. The archwire assembly 56 may be pre-assembled and packaged for delivery to a doctor's office with the sleeve 60 and friction-creating substance 62 already on the archwire 58 and/or sleeve 60. This advantageously eliminates the frustrating and time consuming field assembly required to apply the sleeve 60 onto archwire 58 and limits its movement along archwire 58.

A wide range of friction-creating substances 62 may be used in the invention to increase the sliding resistance of the sleeve 60 along archwire 58. For example, the friction-creating substance may be selected from waxes, sugar compounds, starches, elastomeric materials, organic materials, and polymeric materials. Moreover, these friction-creating materials may advantageously be removable, such as by being water soluble. In this manner, after sleeve 60 is properly positioned and crimped to secure sleeve 60 to archwire 58 in a fixed position, the removable friction-creating substance 62 may be removed by simply washing the archwire 58 or allowing the patient=s saliva to remove the friction-creating substance 62 over time.

Figure 7:
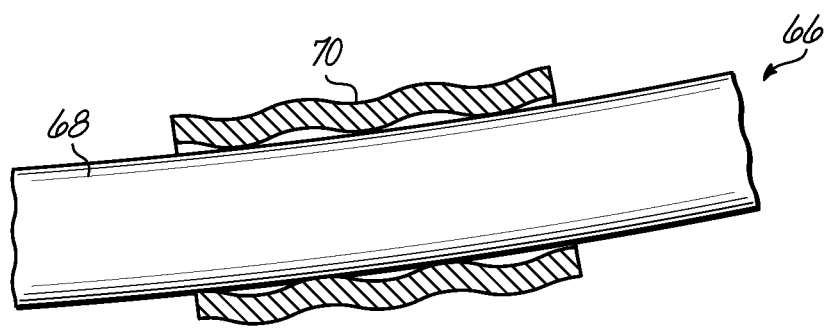
FIG. 7 is an enlarged view of an archwire assembly having a partially crimped sleeve.

FIG. 7 shows yet another embodiment of the invention. FIG. 7 shows an archwire assembly 66 comprising an archwire 68 having a crimpable sleeve 70 partially crimped to limit movement of sleeve 70 along archwire 68. Although archwire assembly 66 includes a partially crimped sleeve 70, the sleeve 70 remains movable along archwire 68 upon the application of a large enough force. Otherwise, the position of sleeve 70 remains stationary. To prevent the unintentional movement of sleeve 70, the force required to move sleeve 70 should be greater than the weight of sleeve 70. For example, sleeve 70 may be adapted to move on the application of a force of approximately one half pound. This prevents the movement of sleeve 70 under its own weight but allows sleeve 70 to be easily repositioned along archwire 68. In this manner, after partially crimped sleeve 70 is properly positioned, sleeve 70 is completely crimped to secure sleeve 70 to archwire 68 in a fixed position. Additionally, archwire assembly 66 may further include removable stops as an additional feature to, for example, prevent sleeve 70 from coming off the archwire 68. A friction-creating substance as described above may also be used in combination with archwire 68 and sleeve 70. The archwire assembly 66 may be pre-assembled and packaged for delivery to a doctor's office with the partially crimped sleeve 70 already mounted on the archwire 68. This advantageously eliminates the frustrating and time consuming field assembly required to apply the sleeve 70 onto archwire 68 and limits its movement along archwire 68.

Figure 8:
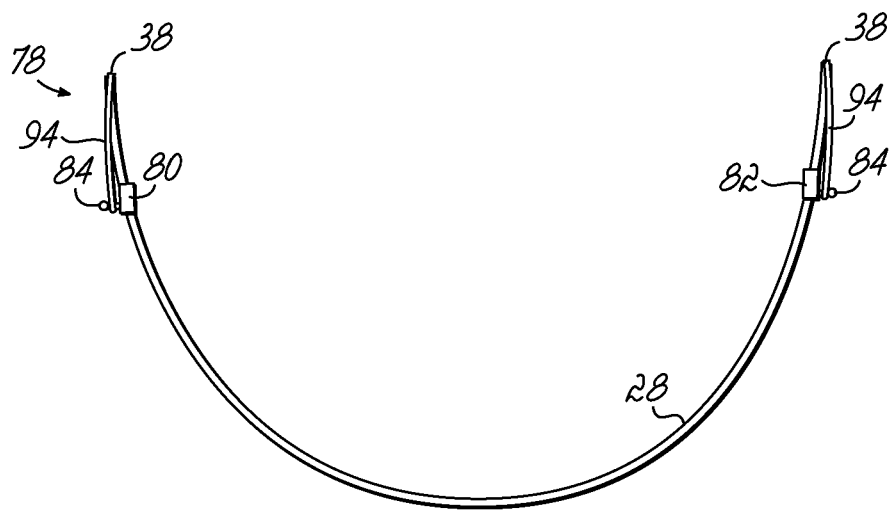
FIG. 8 is a top plan view of an alternative embodiment of an archwire assembly according to the invention.
Figure 9:
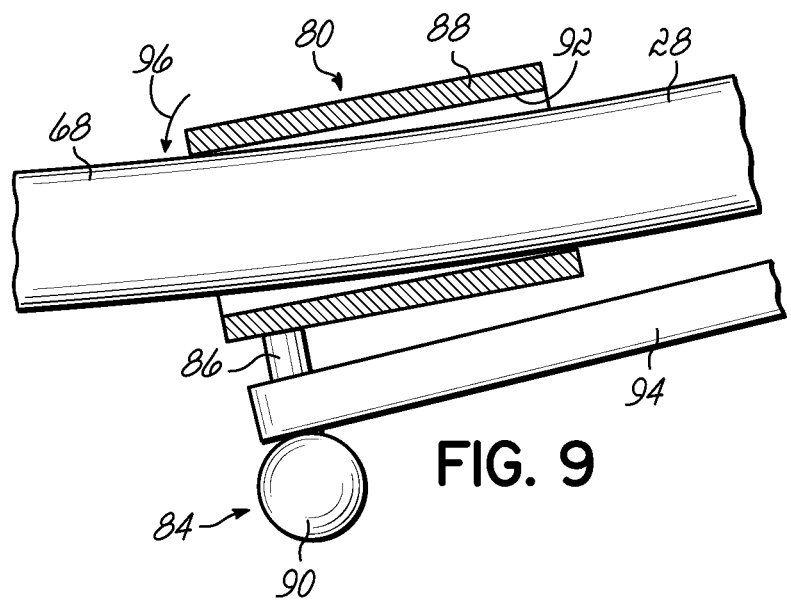
FIG. 9 is an enlarged view in partial cross-section of a portion of FIG. 8.

With reference to FIGS. 8 and 9, an archwire assembly, indicated generally by reference numeral 78, includes a pair of crimpable sleeves 80, 82 each applied in an uncrimped condition to archwire 28 (FIGS. 1-3). Each of the sleeves 80, 82, of which only crimpable sleeve 80 is shown for purposes of description in FIG. 9, features a ball hook 84 with a post 86 projecting from a tubular body 88, a head 90 located at the free end of the post 86, and a lumen 92, through which the archwire 28 is threaded, that is slightly larger in diameter than archwire 28. The sleeves 80, 82 are positioned on the archwire 28 proximate to the free ends 38, 40 of the archwire 28 with the ball hook 84 on each sleeve 80, 82 remote from the corresponding free end 38, 40.

Each of the sleeves 80, 82 is coupled by a removable stop 94, in the form of an endless resilient or elastomeric band, with a corresponding one of the free ends 38, 40 of archwire 28. The head 90 assists in securing the removable stop 94 to each ball hook 94 as the removable stop 94 is looped over the post 86. The elastic force applied by the removable stop 94 to the ball hook 84 creates a torque because the diameter of lumen 93 is larger than the diameter than archwire 28, the elastic force is not parallel to the centerline of the tubular body 88 but spaced radially by post 86, and the ball hook 84 is off-center of the tubular body 88 in a mesial-distal direction. The torque causes the tubular body 88 to rotate, cock or cant relative to the archwire 28, in a direction generally indicated by arrow 96, for securing the tubular body 88 to the archwire 28 in a temporarily position by a frictional engagement between the tubular body 88 and the outer surface of the archwire 28.

The archwire assembly 78 is pre-assembled and packaged for delivery to a doctor's office with the sleeves 80, 82 already mounted and self-locked by one of the removable stops 94 on the archwire 28. The invention contemplates that the archwire assembly 78 may be positioned in association with the braces 10 on one or both of the upper teeth 12 and the lower teeth 14. After the braces 10 are deployed in the patient=s mouth, the removable stops 94 are removed to release the sleeves 80, 82. The sleeves 80, 82 are then freely movable along the archwire 28 until crimped to establish a fixed position. If at least one sleeve 80, 82 is crimped on the braces 10 of the upper teeth 12 in, for example, the upper left quadrant and on the braces 10 of the lower teeth 14 in, for example, the lower left quadrant, a ligature or other resilient member (not shown) may be used to interconnect the ball hooks 84 for applying an orthodontic correction or, alternatively, to achieve intermaxillary fixation following orthognathic surgery. It is contemplated that each of the sleeves 80, 82 may include other types of attachments (not shown).

While the invention has been illustrated by the description of embodiments thereof, and while the embodiments have been described in considerable detail, it is not intended to restrict or in any way limit the scope of the appended claims to such detail. Additional advantages and modifications will readily appear to those skilled in the art. The invention in its broader aspects is, therefore, not limited to the specific details, representative apparatus, and illustrative examples shown and described. Accordingly, departures may be made from such details without departing from the spirit or scope of the general inventive concept.

Having described the invention, what is claimed is:

1. An archwire assembly for orthodontic braces, comprising:
    an archwire;
    a crimpable sleeve positioned on the archwire and including a body having a closed tubular shape in transverse cross-section and including an interior surface, the crimpable sleeve including a first pair of regions of the interior surface in contacting relationship with the archwire on opposite sides thereof and a second pair of regions of the interior surface spaced from and not in contacting relationship with the archwire on opposite sides thereof,
    wherein the crimpable sleeve is moveable on the archwire upon application of a first force on the sleeve in a direction generally parallel to the archwire, the first pair of regions being in contact with the archwire during movement of the crimpable sleeve, the first pair of regions completely resisting movement of the crimpable sleeve along the archwire under the weight of the crimpable sleeve when the archwire and crimpable sleeve are oriented such that a longitudinal axis of a length of the archwire surrounded by the crimpable sleeve is in a vertical orientation, and wherein the crimpable sleeve is capable of being completely crimped to secure it in a fixed position on the archwire.

2. The archwire assembly of claim 1, wherein the first regions are circumferentially spaced from the second regions.

3. The archwire assembly of claim 2, wherein the first regions are diametrically opposed from the second regions.

4. The archwire assembly of claim 1, further comprising a plurality of first pairs of regions in contacting relationship with the archwire and a plurality of second pairs of regions spaced from and not in contacting relationship with the archwire.

5. The archwire assembly of claim 4, wherein contact between the archwire and the first pairs of regions substantially prevents contact between the second pairs of regions and the archwire.

6. The archwire assembly of claim 1, wherein the crimpable sleeve extends along a length and the first and second pairs of regions are alternately distributed along the length.

7. A method of pre-assembling a crimpable sleeve on an archwire and shipping the archwire and crimpable sleeve assembly, the method comprising the steps of:
    providing an archwire,
    providing a crimpable sleeve, the crimpable sleeve having a closed tubular shape in transverse cross-section and including an interior surface,
    sliding the crimpable sleeve on the archwire,
    partially crimping the crimpable sleeve on the archwire such that the crimpable sleeve has a first pair of regions of the interior surface in contacting relationship with the archwire on opposite sides thereof and a second pair of regions of the interior surface spaced from and not in contacting relationship with the archwire on opposite sides thereof, the first pair of regions completely resisting movement of the crimpable sleeve along the archwire under the weight of the crimpable sleeve when the archwire and crimpable sleeve are oriented such that a longitudinal axis of a length of the archwire surrounded by the crimpable sleeve is in a vertical orientation,
    packaging the archwire and crimpable sleeve assembly, and
    shipping the packaged archwire and crimpable sleeve assembly to a destination.

8. A method of receiving and finally assembling a pre-assembled crimpable sleeve and archwire assembly, the crimpable sleeve having a first pair of regions of an interior surface thereof in contacting relationship with the archwire on opposite sides thereof and a second pair of regions of the interior surface spaced from and not in contacting relationship with the archwire on opposite sides thereof, the first pair of regions completely resisting movement of the crimpable sleeve along the archwire under the weight of the crimpable sleeve when the archwire and crimpable sleeve are oriented such that a longitudinal axis of a length of the archwire surrounded by the crimpable sleeve is in a vertical orientation, the method comprising the steps of:
    receiving the pre-assembled crimpable sleeve and archwire assembly,
    moving the crimpable sleeve to a desired location on the archwire; and
    completely crimping the crimpable sleeve on the archwire to secure the sleeve to the archwire at the desired location.

9. The method of claim 8, wherein moving the crimpable sleeve includes sliding the crimpable sleeve.

10. The method of claim 8, wherein moving the crimpable sleeve includes maintaining the first pair of regions in contacting relationship with the archwire.

* * * * *